United States Patent [19]

Hansen

[11] 4,181,659
[45] Jan. 1, 1980

[54] BIS-PENICILLANOYLOXY-ALKANES

[75] Inventor: Kai Hansen, Herlev, Denmark

[73] Assignee: Leo Pharmaceutical Products Ltd. A/S, Ballerup, Denmark

[21] Appl. No.: 783,984

[22] Filed: Apr. 4, 1977

[30] Foreign Application Priority Data

Apr. 15, 1976 [GB] United Kingdom .............. 15746/76

[51] Int. Cl.² .................... A61K 31/43; C07D 499/00; C07D 499/02
[52] U.S. Cl. .................................. 424/271; 542/404; 542/422; 260/239.1; 424/270
[58] Field of Search ......... 260/239.1, 240 G, 306.7 C; 542/404, 422; 424/270, 271

[56] References Cited

U.S. PATENT DOCUMENTS

| | | | |
|---|---|---|---|
| 3,755,588 | 8/1973 | Lund | 260/239.1 |
| 3,869,449 | 3/1975 | Godtfredsen | 260/239.1 |
| 3,957,764 | 5/1976 | Lund | 260/239.1 |

FOREIGN PATENT DOCUMENTS

| | | | |
|---|---|---|---|
| 1303491 | 1/1973 | United Kingdom | 260/239.1 |
| 1405886 | 9/1975 | United Kingdom | 260/239.1 |

OTHER PUBLICATIONS

R. S. Baltimore et al., "Antimicrobial Agents & Chemotherapy," Apr. 1976, pp. 701–705.
J. T. Park et al., "Biochemical & Biophysical Research Communications," vol. 51, No. 4, 1973.
E. Grunberg et al., "Antimicrobial Agents & Chemotherapy," Apr. 1976, pp. 589–594.

*Primary Examiner*—Gerald A. Schwartz
*Attorney, Agent, or Firm*—Dann, Dorfman, Herrell and Skillman

[57] ABSTRACT

The present invention relates to hitherto unknown esters of the below formula I, to salts of the esters of formula I with pharmaceutically acceptable acids, to methods for producing said new compounds, to pharmaceutical compositions containing said new compounds, and to methods of treating patients suffering from infectious diseases using said new compounds.

The compounds of the invention, which are valuable in the human and veterinary practice, have the formula I

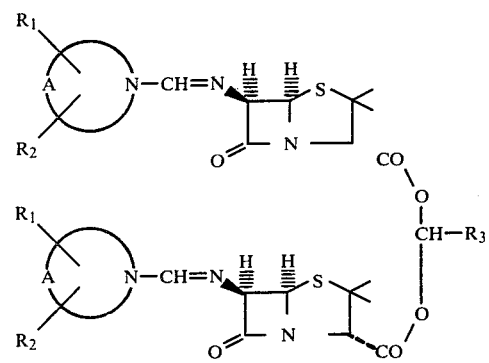

in which
$R_1$ and $R_2$ represent the same or different substituents, and each represents hydrogen or lower alkyl;
A represents a carbon chain having from 5 to 8 carbon atoms, in which optionally an oxygen or a sulphur atom can be substituted for a methylene group; or the grouping

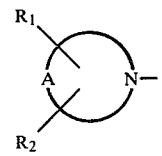

represents a bicyclic system containing from 5 to 10 carbon atoms, or a bicyclic system containing from 4 to 9 carbon atoms, in which optionally an oxygen or a sulphur atom is substituted for a methylene group; or the grouping

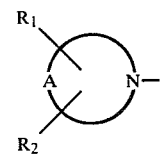

represent a spirocyclic system containing from 7 to 10 carbon atoms;
$R_3$ represents hydrogen or lower alkyl, halogen substituted lower alkyl, and unsubstituted and substituted aryl and aralkyl.

The esters of the present invention are absorbed efficiently when given orally and are non-toxic when given parenterally. After the absorption the esters are converted to the corresponding penicillanic acids by enzymatic hydrolysis. Furthermore, these esters are chemically more stable then the corresponding free acids.

8 Claims, No Drawings

BIS-PENICILLANOYLOXY-ALKANES

The present invention relates to hitherto unknown esters of the below formula I, to salts of the esters of formula I with pharmaceutically acceptable acids, to methods for producing said new compounds, to pharmaceutical compositions containing said new compounds, and to methods of treating patients suffering from infectious diseases, i.e., bacterial infections, using said new compounds.

The compounds of the invention, which are valuable in the human and veterinary practice, have the formula I

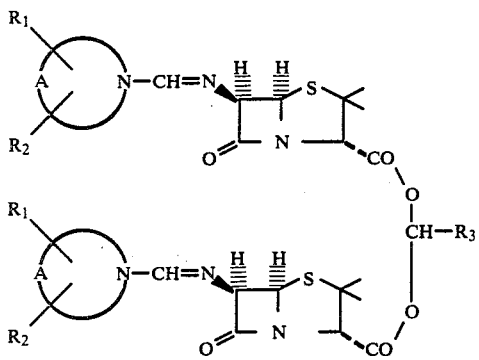

in which $R_1$ and $R_2$ represent the same or different substituents, and each represents hydrogen or lower alkyl, such as methyl, ethyl, propyl, isopropyl, butyl, sec-butyl, tert-butyl, pentyl and hexyl;

A represents a carbon chain having from 5 to 8 carbon atoms, in which optionally an oxygen or a sulphur atom can be substituted for a methylene group; or the grouping

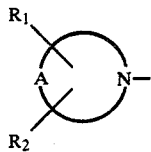

represents a bicyclic system containing from 5 to 10 carbon atoms, such as 3-azabicyclo[3,1,0]hexyl-3, 3-azabicyclo[3,2,0]heptyl-3; 3-azabicyclo[3,3,0]octyl-3, 3-azabicyclo[3,2,2]nonyl-3, 8-azabicyclo[4,3,0]nonyl-8, 4-azabicyclo[5,4,0]undecyl-4 and the corresponding isomers, or a bicyclic system containing from 4 to 9 carbon atoms, in which optionally an oxygen or a sulphur atom is substituted for a methylene group, such as 3-oxa-9-aza-bicyclo[3,2,1]octyl-9 and 3-thia-8-azabicyclo[4,3,0]nonyl-8 and the corresponding isomers and similar ring systems; or the grouping

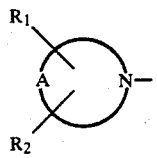

represents a spirocyclic system containing from 7 to 10 carbon atoms, such as 6-azaspiro[2,5]octyl-6, 8-azaspiro[4,5]decyl-8 and 3-azaspiro[5,5]undecyl-3 and similar radicals;

$R_3$ represents hydrogen or lower alkyl, such as methyl, ethyl, propyl, isopropyl, butyl, isobutyl, sec-butyl, tert-butyl, pentyl, neopentyl and hexyl and the corresponding isomers; and halogen substituted lower alkyl, such as chloromethyl, trichloromethyl, trifluoromethyl and 2,2,2-trichloroethyl and similar radicals; and unsubstituted and substituted aryl and aralkyl, the aryl part of which can e.g. be phenyl, 2-fluorophenyl, 3-fluorophenyl, 4-fluorophenyl, 2-chlorophenyl, 3-chlorophenyl, 4-chlorophenyl, 2,6-dichlorophenyl, 2,4,6-trichlorophenyl, 2-hydroxyphenyl, 3-hydroxyphenyl, 4-hydroxyphenyl, 2-methoxyphenyl, 3-methoxyphenyl, 4-methoxyphenyl, 4-ethoxyphenyl, 4-isopropyloxymethyl, 2-tolyl, 3-tolyl, 4-tolyl, 1-naphthyl, 2-naphthyl. More particularly, the grouping

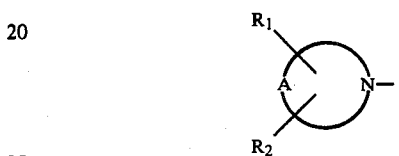

represents piperidyl-1, hexahydro-1H-azepin-1-yl, hexahydro-1(2H)-azocin-1-yl, octahydro-1H-azonin-1-yl, 4-methylpiperidyl-1, 4-ethylpiperidyl-1, 4-methyl-hexahydro-1H-azepin-1-yl, 2,2-dimethylpiperidyl-1, 8-azaspiro[4,5]decyl-8, cis-3-azabicyclo[3,3,0]octyl-3, cis-8-azabicyclo[4,3,0]nonyl-8, morpholinyl-4, thiomorpholinyl-4, and 1-thia-4-azacycloheptyl.

In particular, $R_3$ represents hydrogen, methyl, ethyl, or phenyl, and the grouping

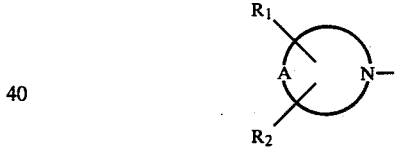

represents 1-piperidyl, hexahydro-1H-azepin-1-yl, hexahydro-1(2H)-azocin-1-yl, or octahydro-1H-azonin-1-yl.

In the above and in the following the expression "lower" in connection with an organic radical indicates a carbon atom content of from 1 to 6.

As stated above, the invention also relates to salts of the esters of formula I with pharmaceutically acceptable non-toxic acids. Suitable acids are the conventional mineral acids, such as the hydrohalide acids, e.g. hydrochloric and hydrobromic acid, phosphoric acid, sulfuric acid, nitric acid, and the conventional organic acids, such as p-toluenesulfonic acid, methanesulfonic acid, formic acid, acetic acid, propionic acid, citric acid, tartaric acid and maleic acid. However, salts with other, in themselves therapeutically active acids, such as penicillins, cephalosporins, and fusidic acid, are also within the scope of the invention.

It is known that certain 6-amidinopenicillanic acids and salts thereof are valuable antibiotics which, however, are poorly absorbed from the gastrointestinal tract. Certain easily hydrolysable esters of 6-amidinopenicillanic acids such as acyloxymethylesters are well absorbed, but are rather toxic when given parenterally.

The esters of the present invention are absorbed efficiently when given orally and are non toxic when given parenterally. After the absorption the esters are converted to the corresponding penicillanic acids by enzymatic hydrolysis. Furthermore, these esters are chemically more stable than the corresponding free acids.

The invention also comprises a method for the preparation of the above described compounds. In a first embodiment 2 moles of a salt of an amidinopenicillanic acid of the below formula II are reacted with 1 mole of a compound of the below formula III according to the below reaction scheme to form the desired compound of formula I:

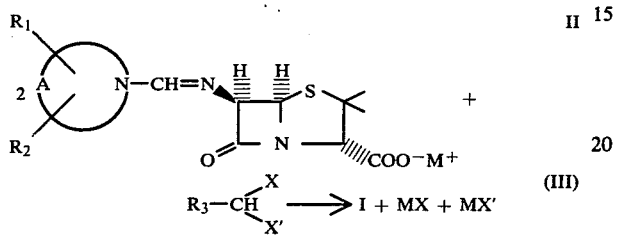

in which formulae $R_1$, $R_2$, $R_3$, and A have the above meanings, $M^+$ is a cation such as $Na^+$, $K^+$, $Ca^{++}$, $NH_4^+$ or $(C_2H_5)_3NH^+$, and X and X' are similar or different leaving groups, such as Cl, Br, I and p-toluenesulfonyloxy.

The reaction is performed in a suitable solvent, e.g. N,N-dimethylformamide, acetone, or hexamethyl phosphoric acid triamide, usually at a temperature from about 0° C. to about 60° C.

In a second embodiment of the method of the invention a 1,1-bis(6-aminopenicillanoyloxy)-alkane of the formula IV

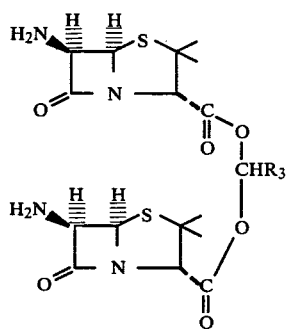

in which $R_3$ has the above meaning, is reacted with 2 moles of a reactive derivative of an amide or thioamide of the formula V

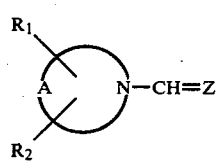

in which $R_1$, $R_2$, and A have the above meanings and Z stands for oxygen or sulphur to yield the desired compound of formula I.

As examples of reactive derivatives of a compound of formula V, the following non-limiting types may be given:

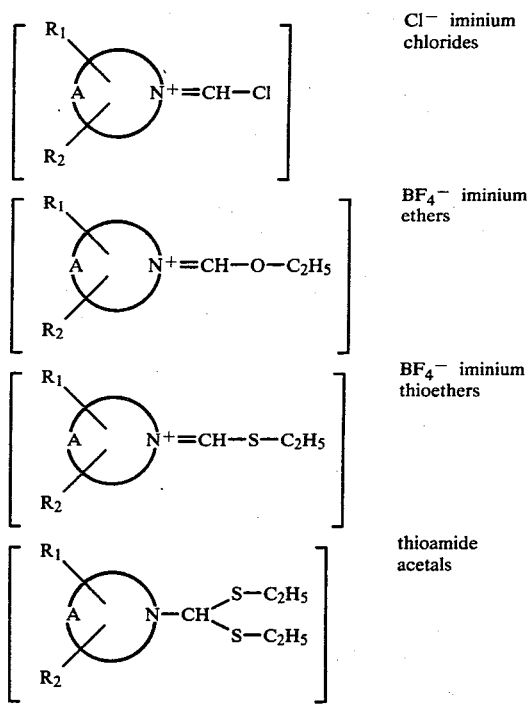

in which $R_1$, $R_2$, and A have the above meanings.

The reactions with the said reactive derivatives are well-known to the man skilled in the art for preparing amidinopenicillanic acid derivatives, confer e.g. British Pat. No. 1,293,590 which also describes in detail the meaning of "a reactive derivative of a compound of formula V."

In a third embodiment compounds of formula I are prepared by reacting a 1,1-bis(6-aminopenicillanoyloxy)-alkane of the above formula IV with a compound of the formula VI

in which X" is a halogen atom, preferably chlorine, Y is an oxygen or a sulphur atom, and $R_4$ is a lower alkyl or benzyl radical, whereby the hydrogen atoms of the 6-amino groups in formula IV are substituted by an $R_4$—O—CM=, or by an $R_4$—O—CH= group. Without isolation of the reaction product, an amine of the formula VII

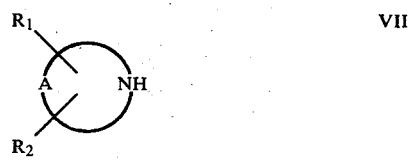

in which $R_1$, $R_2$ and A have the above meanings, is added to the reaction mixture, whereby a component of formula I is obtained.

The reaction is preferably performed in an inert organic solvent such as diethyl ether, tetrahydrofuran, ethyl acetate or benzene at room temperature or lower temperatures. The first part of the reaction proceeds rapidly and after the addition of the amine of formula VII the reaction mixture is placed at room temperature or at lower temperature until the reaction has finished.

In a fourth embodiment an ester of the formula VIII

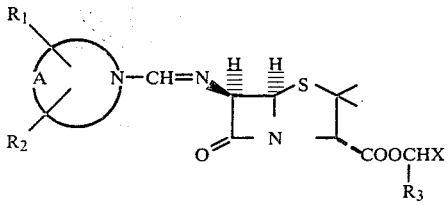

VIII in which formula $R_1$, $R_2$, $R_3$, X, and A are as defined above, is reacted with a salt of the formula II to form the desired compound of formula I.

The reaction is performed in a suitable solvent, e.g. N,N-dimethylformamide, acetone, or hexamethylphosphoric acid triamide, usually at a temperature from about 0° C. to about 60° C.

The starting materials of formulae II, III, IV, V, VI, VII and VIII are known or may be prepared by methods analogous to those used for the preparation of the known compounds.

The reaction products of formula I can be purified and isolated in usual manner and may be obtained either in the free state or in the form of a salt.

It is a further object of the present invention to provide pharmaceutical compositions which are useful in the treatment of infectious diseases in the human and veterinary practice.

With this object in view, the compositions of the invention contain as an active component at least one member selected from the group consisting of compounds of the formula I and salts thereof as defined above, together with solid or liquid pharmaceutical carriers and/or diluents.

In the said compositions, the proportion of therapeutically active material to carrier substance can vary between 1% and 95% by weight. The compositions can be worked up to various pharmaceutical forms of presentation, such as tablets, pills, dragees, suppositories, capsules, sustained-release tablets, suspensions and the like containing the compounds of formula I or their atoxic salts, mixed with carriers and/or diluents.

Pharmaceutically acceptable, non-toxic, organic or inorganic, solid or liquid carriers and/or diluents can be used to make up compositions containing the present compounds. Gelatine, lactose, starch, magnesium stearate, talc, vegetable and animal fats and oils, gum, polyalkylene glycol, buffers or other known carriers and/or diluents for medicaments are all suitable.

Furthermore, the compositions may contain other pharmaceutically active components which can appropriately be administered together with the present compounds in the treatment of infectious diseases, such as other antibacterials.

The compounds of formula I are dibasic and may form salts with one as well as both of the basic moieties. The compounds of formula I are only slightly soluble in water. For use in injection medicine it is preferred to use a salt of the compound of formula I, e.g. the dihydrochloride.

As indicated above, the present compounds may be worked up to pharmaceutical forms of presentation including suspensions and non-aqueous ointments and creams. A pharmaceutical preparation for oral treatment may be in the form of a suspension of one of the present compounds, the preparation containing from 10 to 100 mg per ml of a non-aqueous vehicle.

Another object of the invention resides in the selection of a dose of the compounds of the invention which dose can be administered so that the desired activity is achieved without simultaneous secondary effects. In the human therapy, the present compounds are conveniently administered (to adults) in dosage units containing not less than 50 mg and up to 2500 mg, preferably from 250 to 1000 mg, calculated as the compound of formula I.

By the term "dosage unit" is meant a unitary, i.e. a single dose which is capable of being administered to a patient, and which may be readily handled and packed, remaining as a physically stable unit dose comprising either the active material as such or a mixture of it with solid or liquid pharmaceutical diluents, carriers, solvents and/or auxiliary agents.

In the form of a dosage unit, the compound may be administered once or more times a day at appropriate intervals, always depending, however, on the condition of the patient, and in accordance with the prescription made by the medical practitioner.

Thus a daily dose will preferably be an amount of from 0.25 to 5 g of a compound of formula I or an equivalent amount of a salt thereof as defined before, administered 2-4 times daily.

If the composition is to be injected, a sealed ampoule, a vial or a similar container may be provided containing a parenterally acceptable aqueous or oily injectable solution or dispersion of the active material as the dosage unit.

The parenteral preparations are in particular useful in the treatment of conditions in which a quick response to the treatment is desirable. In the continuous therapy of patients suffering from infectious diseases, the tablets or capsules may be the appropriate form of pharmaceutical preparation owing to the prolonged effect obtained when the drug is given orally, in particular in the form of sustained-release tablets.

In the treatment of infectious diseases, such tablets may advantageously contain other active components, as mentioned hereinbefore, in particular penicillins or cephalosporins, which show a synergistic action with amidinopenicillanic acids.

Still another object of the invention is to provide a method of treating patients suffering from infectious diseases, the method comprising administering to adult patients from 0.25 g to 5 g per day of a compound of the formula I or an equivalent amount of a salt or an ester as defined before of a compound of the formula I. Preferably, the compound is given in the form of the dosage units aforesaid.

The invention will be further described in the following Examples which are not to be construed as limiting the invention.

EXAMPLE 1

Bis(6-[(hexahydro-1H-azepin-1-yl)-methyleneamino]-penicillanoyloxy)-methane,dihydrochloride To a suspension of sodium 6-[(hexahydro-1H-azepin-1-yl)-methyleneamino]-penicillanate (6.94 g) in N,N-dimethylformamide (70 ml), chloroiodomethane (1.76 ml) was added and the reaction mixture was stirred for 144 hours at room temperature. Ethyl acetate (250 ml) was added and the mixture was extracted with water (4×50 ml) and saturated aqueous sodium chloride (25 ml). Water (100 ml) was added and the apparent pH value of the stirred mixture was adjusted to 2.5 by addition of 4 N hydrochloric acid. The aqueous phase was separated, washed with ether (25 ml), filtered and freeze-dried to give an amorphous product, which was crystallized from water/propanol-2, melting point 198°–200° C.

The IR-spectrum (KBr) showed strong bands at: 1790, 1765 and 1680 cm$^{-1}$.

The NMR-spectrum (D$_2$O) showed signals at: $\delta = 1.58$ (s), 1.64 (s), 1.5–2.1 (m), 3.5–3.9 (m), 4.78 (s), 5.56 (d, J=4), 5.72 (d, J=4), 6.03 (bs), 8.06 (bs) ppm.

Standard: 3-Trimethylsilyl-propanesulfonic acid sodium salt was used as internal reference.

EXAMPLE 2

Bis(6-[(hexahydro-1H-azepin-1-yl)-methyleneamino]-penicillanoyloxy)-methane

The dihydrochloride obtained according to Example 1 was dissolved in water, ethyl acetate was added, and a sodium hydrogen carbonate solution was added while stirring until pH in the aqueous solution was about 7. The organic phase was separated, dried, and evaporated in vacuum leaving the title compound as a yellow oil, which crystallized from ether on cooling. M.p. 127°–131° C. dec.

EXAMPLE 3

Bis(6-[(hexahydro-1H-azepin-1-yl)-methyleneamino]-penicillanoyloxy)-methane, dihydrochloride To an ice-cold solution of 1-thioformyl-hexamethyleneimine (1.43 g) in dry methylene chloride (20 ml), triethyloxonium tetrafluoroborate (1.90 g) was added. The solution was stirred for half an hour at room temperature and again cooled in an ice-bath. An ice-cold solution of bis(6-aminopenicillanoyloxy)-methane (2.22 g) and N,N-diisopropylethylamine (1.80 ml) in dry methylene chloride (20 ml) was added, and the reaction mixture was slowly concentrated in vacuo at about 0° C. After about 3 hours all the solvent was evaporated off. The residue was extracted with diethyl ether (3×100 ml) and the diethyl ether extract was dried and treated with charcoal. Water (100 ml) was added, the apparent pH-value was adjusted to 2.5 by addition of 4 N hydrochloric acid and the aqueous phase was freeze-dried to give an amorphous powder, which was crystallized from methanol/propanol-2 to give a product, the NMR-spectrum of which was identical with that described in Example 1.

EXAMPLE 4

Bis(6-[(hexahydro-1H-azepin-1-yl)-methyleneamino]-penicillanoyloxy)-methane, dihydrochloride To a solution of bis(6-aminopenicillanoyloxy)-methane (2.22 g) and triethylamine (3.2 ml) in dry, alcohol-free chloroform (10 ml), 1-chloromethylenehexamethyleneiminium chloride (2.0 g) in dry alcohol-free chloroform (10 ml) was added dropwise at a temperature of about −20° C. After standing for half an hour at −20° C., the temperature was raised to 0° C. within 15 minutes. The solution was evaporated in vacuo. The residue was stirred with diethyl ether (150 ml), and undissolved triethylamine hydrochloride was filtered off. Water (50 ml) was added, the apparent pH-value was adjusted to 2.5 by addition of 4 N hydrochloric acid and the aqueous phase was freeze-dried to give an amorphous powder, which was crystallized from methanol/propanol-2 to give a product, the NMR-spectrum of which was identical with that described in Example 1.

EXAMPLE 5 TO 26

By following the procedure of Example 3 (method B) or Example 4 (method C), the compounds of Table I were obtained.

Table 1

| Ex. No. | R$_2$ | Method |
|---|---|---|
| 5 | piperidyl-1 | C |
| 6 | 2-methylpiperidyl-1 | C |
| 7 | 3-methylpiperidyl-1 | C |
| 8 | 4-methylpiperidyl-1 | C |
| 9 | 4-ethylpiperidyl-1 | B |
| 10 | 4,4-dimethylpiperidyl-1 | B |
| 11 | 2,6-dimethylpiperidyl-1 | C |
| 12 | 2-methyl-hexahydro-1H-azepin-1-yl | B |
| 13 | 3-methyl-hexahydro-1H-azepin-1-yl | B |
| 14 | 4-methyl-hexahydro-1H-azepin-1-yl | B |
| 15 | hexahydro-1(2H)-azocin-1-yl | C |
| 16 | octahydro-1H-azonin-1-yl | C |
| 17 | 8-azaspiro[4,5]decyl-8 | B |
| 18 | 3-azaspiro[5,5]undecyl-3 | B |
| 19 | cis-3-azabicyclo[3,3,0]octyl-3 | B |
| 20 | cis-8-azabicyclo[4,3,0]nonyl-8 | B |
| 21 | 3-azabicyclo[3,2,2]nonyl-3 | C |
| 22 | morpholinyl-4 | C |
| 23 | 2-methylmorpholinyl-4 | B |
| 24 | 3-oxa-9-aza-bicyclo-[3,2,1]octyl-9 | B |
| 25 | thiomorpholinyl-4 | B |
| 26 | 1-thia-4-aza-cycloheptyl-4 | B |

Preparation of starting materials for Examples 3–26 (the preparations being numbered in accordance with the examples for which they are used).

PREPARATION 3 B

1-Thioformyl-hexamethyleneimine

A solution of hexamethyleneimine (9.92 g) in diethyl ether (100 ml) was cooled in an ice-bath. Ethyl thioformate (10 ml) was slowly added, and the mixture was stirred for 18 hours at room temperature. The diethyl ether was evaporated off and the residue distilled in vacuo. Bp. 89°–90° C. 0.1 mm Hg.

By following the procedure of Preparation 3 B, the compounds of Table II were obtained,

Table II

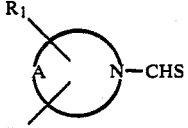

| Prep. No. | $R_2$ | Melting point |
|---|---|---|
| 9 B | 1-Thioformyl-4-ethyl-piperidine | oil[1] |
| 10 B | 1-Thioformyl-4,4-dimethyl-piperidine | 70°–74° C. |
| 12 B | 1-Thioformyl-2-methyl-hexamethyleneimine | oil[1] |
| 13 B | 1-Thioformyl-3-methyl-hexamethyleneimine | oil[1] |
| 14 B | 1-Thioformyl-4-methyl-hexamethyleneimine | oil[1] |
| 17 B | 8-Thioformyl-8-azaspiro[4,5]decane | 46°–50° C. |
| 18 B | 3-Thioformyl-3-azaspiro[5,5]undecane | 66°–69° C. |
| 19 B | 3-Thioformyl-cis-3-azabicyclo[3,3,0]octane | oil[1] |
| 20 B | 8-Thioformyl-cis-8-azabicyclo[4,3,0]nonane | 51°–53° C. |
| 23 B | 4-Thioformyl-2-methyl-morpholine | 120–1 1 mm Hg |
| 24 B | 9-Thioformyl-3-oxa-9-azabicyclo[3,2,1]octane | 69°–70° C. |
| 25 B | 4-Thioformyl-thiomorpholine | 97°–98° C. |
| 26 B | 4-Thioformyl-1-thia-4-azacycloheptane | 34°–35° C. |

[1]Obtained by evaporation of the reaction mixture; sufficiently pure for use in the next step without further purification.

PREPARATION 4 B

1-Chloromethylenehexamethyleneiminium chloride

1-Formylhexamethyleneimine (12.7 g) was dissolved in dry diethyl ether (250 ml). While stirring and cooling oxalyl chloride (8.5 ml) in dry diethyl ether (50 ml) was added dropwise, and the mixture was stirred overnight at room temperature. The precipitated iminium chloride was filtered off, washed with dry diethyl ether, and placed in an exiccator.

The starting material, 1-formylhexamethyleneimine, was prepared from hexamethyleneimine and chloral, confer e.g. British Pat. No. 1,293,590.

Following the procedure of Preparation 4 B the following compounds were obtained:

1-chloromethylenepiperidinium chloride
1-chloromethylene-2-methyl-piperidinium chloride
1-chloromethylene-3-methyl-piperidinium chloride
1-chloromethylene-4-methyl-piperidinium chloride
1-chloromethylene-2,6-dimethyl-piperidinium chloride
1-chloromethylene-hexahydro-1(2H)-azocinium chloride
1-chloromethylene-octahydro-1H-azoninium chloride
4-chloromethylene-morpholinium chloride
3-chloromethylene-3-azabicyclo[3,2,2]nonanium chloride

PREPARATION 20 C

Cis-8-azabicyclo[4,3,0]nonane

To a slurry of lithium aluminium hydride (17.1 g) in dry diethyl ether (375 ml) under a nitrogen atmosphere, cis-hexahydrophthalimide (23.0 g) in dry tetrahydrofuran (300 ml) was added over a two-hour period. The mixture was refluxed for 2.5 hours, cooled and treated very slowly with excess of water. The precipitate was filtered off and the filtrate was evaporated to yield the title compound as a viscous oil, which was used in the next step without purification.

EXAMPLE 27

Bis(6-[(hexahydro-1H-azepin-1-yl)-methyleneamino]-penicillanoyloxy)-methane, dihydrochloride To a suspension of sodium 6-[(hexahydro-1H-azepin-1-yl)-methyleneamino]-penicillanate (6.94 g) in N,N-dimethylformamide (70 ml), diiodomethane (5.0 ml) was added, and the reaction mixture was stirred for 48 hours at room temperature. The product was isolated by following the procedure of Example 1 to give a product, the NMR-spectrum of which was identical with that described in Example 1.

EXAMPLE 28

Bis(6-[(hexahydro-1H-azepin-1-yl)-methyleneamino]-penicillanoyloxy)-methane, dihydrochloride To a solution of bis(6-aminopenicillanoyloxy)-methane (4.4 g) in dry ethyl acetate (100 ml), isopropyl formimidate hydrochloride (2.5 g) was added. The suspension was stirred for half an hour at room temperature and then cooled in an ice-bath. Hexamethyleneimine (2.2 ml) was added, the reaction mixture was kept at 0° C. overnight and thereafter filtered. Water (100 ml) was added to the filtrate, and the apparent pH value of the mixture was adjusted to 2.5 by addition of 4 N hydrochloric acid. The aqueous phase was separated and freeze-dried to give an amorphous powder, which was crystallized from methanol/propanol-2 to yield a product identical with that described in Example 1.

EXAMPLE 29

Bis(6-[(hexahydro-1H-azepin-1-yl)-methyleneamino]-penicillanoyloxy)-methane, dihydrochloride To a solution of bis(6-aminopenicillanoyloxy)-methane (2.22 g) and N,N-diisopropylethylamine (1.7 ml) in dry chloroform (35 ml) at 0° C., N-formylhexamethyleneiminedimethyl sulphate complex (2.5 g) was added, and the reaction mixture was stirred for 20 hours at room temperature. The solution was evaporated, the residue was taken up in ether (200 ml) and the precipitate was filtered off. Water (100 ml) was added, the apparent pH value was adjusted to 2.5 by addition of 4 N hydrochloric acid, and the aqueous phase was separated and freeze-dried to give an amorphous powder, which crystallized from methanol/propanol-2 to give a product identical with that described in Example 1.

EXAMPLE 30

Bis(6-[(hexahydro-1H-azepin-1-yl)-methyleneamino]-penicillanoyloxy)-methane, dihydrochloride To a solution of chloromethyl 6-[(hexahydro-1H-azepin-1-yl)-methyleneamino]-penicillanate (3.94 g) in N,N-dimethylformamide (50 ml), sodium 6-[(hexahydro-1H-azepin-1-yl)-methyleneamino]-penicillanate (3.5 g) was added. The reaction mixture was stirred for 48 hours at room temperature and then diluted with ethyl acetate (150 ml) and extracted with water (4×25 ml). Water (50 ml) was added to the organic phase, and the pH value of the aqueous phase was adjusted to 2.5 by addition of 4 N hydrochloric acid. The aqueous phase was isolated and freeze-dried to yield the desired compound as an amorphous powder, which crystallized from methanol/propanol-2 to give a product identical with that described in Example 1.

The starting material was prepared as follows:

Chloromethyl-6-[(hexahydro-1H-azepin-1-yl)-methyleneamino]-penicillanate hydrochloride.

To a solution of 6-[(hexahydro-1H-azepin-1-yl)methyleneamino]-penicillanic acid (32.5 g) and dry triethylamine (20 ml) in N,N-dimethylformamide (150 ml), chloroiodomethane (70 ml) was added, and the mixture was stirred for 2 hours. Water (450 ml) was added and the organic layer was separated. The aqueous phase was extracted with ether (4×150 ml) and the combined organic phases were extracted with water (2×100 ml), phosphate buffer pH 5.5 (2×300 ml) and water (100 ml). To the organic phase, water (200 ml) was added and the apparent pH value of the mixture was adjusted to 2.5 with 4 N hydrochloric acid. The aqueous phase was isolated and freeze-dried to afford an amorphous powder, which crystallized from methanol/ether.

The IR-spectrum (KBr) showed strong bands at 1780, 1750, and 1680 cm$^{-1}$.

The NMR-spectrum (CD$_3$OD) showed signals at $\delta = 1.60$ (s), 1.76 (s), 1.5–2.2 (m), 3.5–4.0 (m), 4.64 (s), 5.58 (d, J=4), 5.70 (d, J=4), 5.85 (d, J=6.5), 5.99 (d, J=6.5), 8.23 (bs) ppm.

TMS was used as internal standard.

EXAMPLE 31

1,1-Bis(6-[(hexahydro-1H-azepin-1-yl)-methyleneamino]penicillanoyloxy)-ethane

To a solution of 1-chloro-1-iodo-ethane (1.0 ml) in N,N-dimethylformamide (50 ml), sodium 6-[(hexahydro-1H-azepin-1-yl)-methyleneamino]-penicillanate (3.47 g) was added, and the mixture was stirred at 40° C. for 24 hours. Ethyl acetate (200 ml) was added and the mixture extracted with water (4×25 ml) and saturated aqueous sodium chloride (25 ml). The organic phase was dried and evaporated in vacuo to leave a dark oil which was purified by chromatography on Sephadex ® to give the desired compound as a yellow oil.

The IR-spectrum (CHCl$_3$) showed strong bands at: 1760 and 1625 cm$^{-1}$.

The NMR-spectrum (CDCl$_3$) showed signals at $\delta = 1.67$ (s); 1.58 (s); 1.58 (d, J=6); 1.3–2.0 (m); 3.1–3.6 (m); 4.35 (s); 5.08 (bd, J=4); 5.45 (m); 6.90 (q, J=6); 7.60 (s) ppm.

TMS was used as internal standard.

EXAMPLE 32

α,α-Bis(6-[(hexahydro-1H-azepin-1-yl)-methyleneamino]penicillanoyloxy)-toluene

A mixture of sodium iodide (6.0 g), benzal chloride (6.35 ml) and N,N-dimethylformamide (50 ml) was stirred for 18 hours at 40° C. Then sodium 6-[(hexahydro-1H-azepin-1-yl)-methyleneamino]-penicillanate (3.47 g) was added, and the reaction mixture was stirred for further 24 hours at 40° C. The mixture was diluted with ethyl acetate (200 ml) and extracted with water (4×25 ml). To the organic phase, water (100 ml) was added, and the pH-value of the aqueous phase was adjusted to 2.5 by addition of 4 N hydrochloric acid. The aqueous phase was isolated and fresh ethyl acetate (50 ml) was added. Then the apparent pH-value of the mixture was adjusted to 7.5 by addition of saturated aqueous sodium bicarbonate, and the organic phase was isolated, dried, and evaporated in vacuo to leave a residue, which after chromatography Sephadex ® yielded the desired compound as a yellow oil.

The NMR-spectrum (CDCl$_3$) showed signals at $\delta = 1.63$ (s); 1.72 (s); 1.3–2.0 (m); 3.1–3.8 (m); 4.42 (s); 5.10 (d, J=4); 5.50 (m); 7.5 (m); 7.77 (s) ppm.

TMS was used as internal standard.

EXAMPLE 33

1,1-Bis(6-[(hexahydro-1H-azepin-1-yl)-methyleneamino]penicillanoyloxy)-ethane

To an ice-cold solution of 1-thioformyl-hexamethyleneimine (1.43 g) in dry methylene chloride (20 ml) triethyloxonium tetrafluoroborate (1.90 g) was added. The solution was stirred for half an hour at room temperature and again cooled in an ice-bath. An ice-cold solution of 1,1-bis(6-aminopenicillanoyloxy)-ethane (2.29 g) and N,N-diisopropylethylamine (1.80 ml) in dry methylene chloride (20 ml) was added, and the reaction mixture was slowly concentrated in vacuo at about 0° C. After about 3 hours all the solvent was evaporated off. The residue was extracted with diethyl ether (3×100 ml), and the ether extract was dried, treated with charcoal and evaporated in vacuo to yield a yellow oil, the NMR-spectrum of which was identical with that described in Example 31.

EXAMPLE 34 to 51

By following the procedure of Example 33, the compounds of Table III are obtained by using the corresponding 1,1-bis(6-aminopenicillanoyloxy)-alkanes as starting material.

Table III

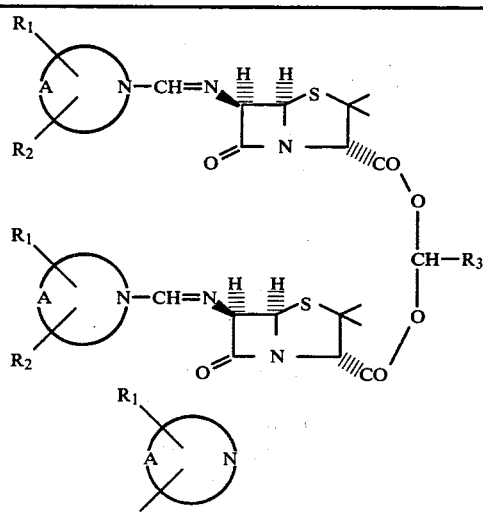

| Ex. No. | R$_2$ | R$_3$ |
|---|---|---|
| 34 | hexahydro-1H-azepin-1-yl | ethyl |
| 35 | " | propyl |
| 36 | " | isopropyl |
| 37 | " | n-butyl |
| 38 | " | isobutyl |
| 39 | " | sec-butyl |
| 40 | " | tert-butyl |
| 41 | " | neopentyl |
| 42 | " | n-hexyl |
| 43 | " | phenyl |
| 44 | " | 3-fluorophenyl |
| 45 | " | 2-chlorophenyl |
| 46 | " | 4-chlorophenyl |
| 47 | " | 2,6-dichlorophenyl |
| 48 | " | 2,4,6-trichlorophenyl |
| 49 | " | 2-naphthyl |
| 50 | " | 2-hydroxyphenyl |

Table III-continued

Structures with R₁, R₂, A, N-CH=N, H H, S, O, N, CO, O, CH-R₃ groups shown.

| Ex. No. | R₂ | R₃ |
|---|---|---|
| 51 | " | 4-methoxyphenyl |

Preparation of starting materials for Examples 33 to 51 (the preparations being numbered in accordance with the example for which they are used).

PREPARATION 33 B 1,1-Bis(6-aminopenicillanoyloxy)-ethane

To a stirred solution of phosphorus pentachloride (1.28 g) in dry alcohol-free chloroform (30 ml), quinoline (1.46 g) was added. The mixture was cooled to $-10°$ C. and 1,1-bis(6-phenylacetamido-penicillanoyloxy)-ethane (1.38 g) was added. After stirring for 15 minutes at $-10°$ C., propanol-1 (6.6 ml) was added and the temperature was kept at $-10°$ C. for a further 15 minutes. Then the mixture was poured into water (50 ml) and petroleumether (110 ml) was added.

The aqueous phase was separated, the pH adjusted to 7.5 by addition of sodium bicarbonate, and the mixture extracted with ethyl acetate (3×25 ml). The organic phases were collected, dried, and evaporated in vacuo to yield a mixture of the desired compound and quinoline. Extraction of the residue with petroleumether (3×20 ml) removed the quinoline and left the desired compound as a yellow oil which was crystallized from chloroform/hexane. The NMR-spectrum (CDCl₃) showed signals at: $\delta=1.57$ (s); 1.60 (d,J=7); 1.67 (s); 1.85 (s); 4.38 (s); 4.60 (d,J=4); 5.52 (m); 6.93 (q,J=7)ppm. TMS was used as internal standard.

By following the procedure of Preparation 33 B, the following compounds are obtained from the corresponding 1,1-bis(6-phenylacetamido-penicillanoyloxy)-alkanes.

- 34 B  1,1-bis(6-aminopenicillanoyloxy)-propane
- 35 B  1,1-bis(6-aminopenicillanoyloxy)-butane
- 36 B  1,1-bis(6-aminopenicillanoyloxy)-2-methylpropane
- 37 B  1,1-bis(6-aminopenicillanoyloxy)-pentane
- 38 B  1,1-bis(6-aminopenicillanoyloxy)-3-methylbutane
- 39 B  1,1-bis(6-aminopenicillanoyloxy)-2-methylbutane
- 40 B  1,1-bis(6-aminopenicillanoyloxy)-2,2-dimethylpropane
- 41 B  1,1-bis(6-aminopenicillanoyloxy)-3,3-dimethylbutane
- 42 B  1,1-bis(6-aminopenicillanoyloxy)-heptane
- 43 B  α,α-bis(6-aminopenicillanoyloxy)-toluene
- 44 B  α,α-bis(6-aminopenicillanoyloxy)-3-fluoro-toluene
- 45 B  α,α-bis(6-aminopenicillanoyloxy)-2-chloro-toluene
- 46 B  α,α-bis(6-aminopenicillanoyloxy)-4-chloro-toluene
- 47 B  α,α-bis(6-aminopenicillanoyloxy)-2,6-dichloro-toluene
- 48 B  α,α-bis(6-aminopenicillanoyloxy)-2,4,6-trichloro-toluene
- 49 B  2-(bis(6-aminopenicillanoyloxy)-methyl)-naphthalene
- 50 B  α,α-bis(6-aminopenicillanoyloxy)-2-hydroxy-toluene
- 51 B  α,α-bis(6-aminopenicillanoyloxy)-4-methoxy-toluene

PREPARATION 33 C 1,1-Bis(6-phenylacetamido-penicillanoyloxy)-ethane

A mixture of sodium iodide (6.0 g), 1,1-dichloroethane (4.3 ml) and N,N-dimethylformamide (30 ml) was stirred for 18 hours at 100° C. Then the reaction mixture was cooled to 40° C. and sodium benzylpenicillinate (3.50 g) was added. After stirring for 44 hours at 40° C. the mixture was diluted with ethyl acetate (100 ml) and extracted with water (2×25 ml), saturated aqueous sodium bicarbonate (20 ml) and water (25 ml). The organic phase was dried and evaporated in vacuo. The residue was extracted with petroleumether (3×50 ml) to leave a dark, viscous oil, which was purified by dry column chromatography on silica gel (eluent: cyclohexan/ethyl acetate 1:1) to yield the desired compound as a yellow foam.

The IR-spectrum (CHCl₃) showed strong bands at: 1780, 1675 and 1495 cm$^{-1}$.

The NMR-spectrum (CDCl₃) showed signals at $\delta=1.43$ (s); 1.54 (d, J=6); 3,63 (s); 4.34 (s); 5.55 (m) 6.17 (d, J=8.5); 6.87 (q, J=6); 7.30 (m) ppm.

TMS was used as internal standard.

PREPARATION 33 D 1,1-Bis(6-phenylacetamido-penicillanoyloxy)-ethane

To a solution of 1-chloro-1-iodo-ethane (1.0 ml) in N,N-dimethylformamide (30 ml), sodium benzylpenicillinate (3.50 g) was added, and the mixture was stirred at 40° C. for 48 hours. Then ethyl acetate (100 ml) was added and the mixture was extracted with water (2×25 ml), saturated aqueous sodium bicarbonate (20 ml) and water (2×25 ml). The organic phase was dried and evaporated in vacuo to give a dark oil, which after purification by dry column chromatography yielded a yellow oil, the NMR-spectrum of which was identical with that described in Preparation 33 C.

PREPARATION 43 C

α,α-Bis(6-phenylacetamido-penicillanoyloxy)-toluene

A mixture of sodium iodide (6.0 g), benzal chloride (6,35 ml) and N,N-dimethylformamide (50 ml) was stirred for 18 hours at 40° C. Then sodium benzylpenicillinate (3.50 g) was added and the reaction mixture was stirred for further 22 hours at 40° C. The mixture was diluted with ethyl acetate (200 ml) and extracted with water (2×50 ml), saturated aqueous sodium bicarbonate (50 ml) and water (50 ml). The organic phase was dried and evaporated in vacuo. The residue was extracted with petroleumether (3×50 ml) to leave a dark oil, which was purified by dry column chromatography on silica gel (eluent:cyclohexan/ethyl acetate 1:1) to yield the desired compound as a yellow oil.

The NMR-spectrum (CDCl$_3$) showed signals at δ=1.38 (s); 1.43 (s); 3.65 (s); 4.42 (s); 5.60 (m); 6.27 (d, J=8), 7.40 (m); 7.72 (s) ppm.

TMS was used as internal standard.

PREPARATION 34 C TO 51 C

By following the procedure of Preparation 33 C, Preparation 33 D or Preparation 43 C, the compounds of Table IV are obtained.

Table IV

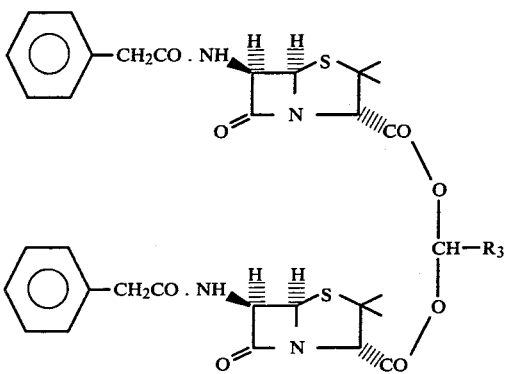

| Prep. No. | R$_3$ | Starting material | Prepared according to Prep. No. |
|---|---|---|---|
| 34 C | ethyl | 1-bromo-1-iodo-propane | 33 D |
| 35 C | propyl | 1,1-dibromobutane | 33 D |
| 36 C | isopropyl | 1,1-dichloro-2-methylpropane | 33 C |
| 37 C | n-butyl | 1,1-dichloropentane | 33 C |
| 38 C | isobutyl | 1,1-dichloro-3-methylbutane | 33 C |
| 39 C | sec-butyl | 1,1-dichloro-2-methylbutane | 33 C |
| 40 C | tert-butyl | 1,1-dibromo-2,2-dimethylpropane | 33 D |
| 41 C | neopentyl | 1,1-dichloro-3,3-dimethylbutane | 33 C |
| 42 C | n-hexyl | 1,1-dichloroheptane | 33 C |
| 44 C | 3-fluoro phenyl | α,α-dichloro-3-fluoro-toluene | 43 C |
| 45 C | 2-chloro phenyl | 2,α,α-trichloro-toluene | 43 C |
| 46 C | 4-chloro-phenyl | 4,α,α-trichloro-toluene | 43 C |
| 47 C | 2,6-dichloro-phenyl | 2,6,α,α-tetrachloro-toluene | 43 C |
| 48 C | 2,4,6-tri-chlorophenyl | 2,4,6,α,α-pentachloro-toluene | 43 C |
| 49 C | 2-naphthyl | 2-dichloromethyl-naphthalene | 43 C |
| 50 C | 2-hydroxy-phenyl | α,α-dichloro-2-hydroxy-toluene | 43 C |
| 51 C | 4-methoxy-phenyl | α,α-dichloro-4-methoxy-toluene | 43 C |

What I claim is:

1. Bis(6-[hexahydro-1H-azepin-1-yl)methyleneamino]-penicillanoyloxy)-methane and stable salts thereof with conventional, non-toxic, pharmaceutically acceptable acids, said salt having a stability greater than the stability of the corresponding salt of free 6-[(hexahydro-1H-azepin-1-yl)-methyleneamino]-penicillanic acid.

2. Bis(6-[(hexahydro-1H-azepin-1-yl)-methyleneamino]-penicillanoyloxy)-methane.

3. A salt of the compound of claim 1 wherein the pharmaceutically acceptable acid is selected from the group consisting of mineral acids and organic acids selected from the group consisting of p-toluenesulfonic acid, methane-sulfonic acid, formic acid, acetic cid, propionic acid, citric acid, tartaric acid and maleic acid.

4. A salt of the compound of claim 3 wherein the mineral acid is selected from the group consisting of hydrochloric acid, hydrobromic acid, phosphoric acid, sulfuric acid and nitric acid.

5. A salt of the compound of claim 3 wherein the mineral acid is a hydrohalide acid.

6. A salt of the compound of claim 5 wherein the hydrohalide acid is hydrochloric acid.

7. A method of treating a patient suffering from a bacterial infection, comprising administering to the patients from 0.25 to 5 g per day bis(6-[(hexahydro-1H-azepin-1-yl)-methyleneamino]-penicillanoyloxy)-methane or a salt thereof as defined in claim 1.

8. A method as defined in claim 7 in which the daily dose is from 1 to 3 g.

* * * * *

UNITED STATES PATENT AND TRADEMARK OFFICE
CERTIFICATE OF CORRECTION

PATENT NO. : 4,181,659
DATED : January 1, 1980
INVENTOR(S) : Kai Hansen

It is certified that error appears in the above-identified patent and that said Letters Patent are hereby corrected as shown below:

The "Assignee" designation "Leo Pharmaceutical Products Ltd. A/S, Ballerup, Denmark" should read --Leo Pharmaceutical Products Ltd. A/S (Lovens kemiske Fabrik Produktionsaktieselskab) Ballerup, Denmark--.

In the Abstract:

The structure of formula I

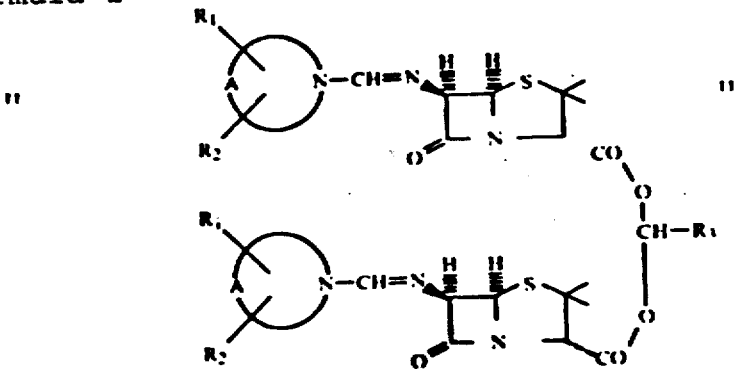

should appear as follows:

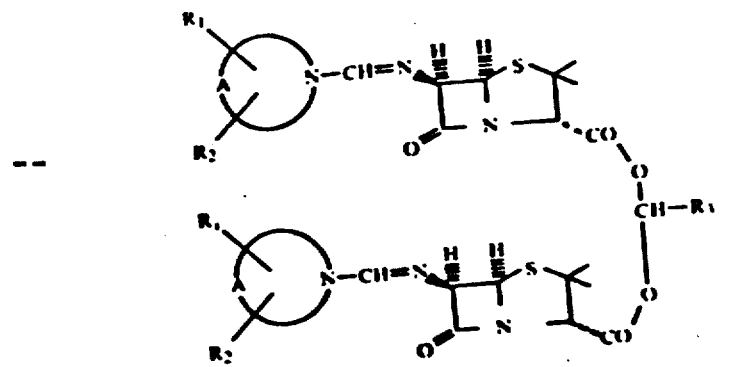

UNITED STATES PATENT AND TRADEMARK OFFICE
CERTIFICATE OF CORRECTION

PATENT NO. : 4,181,659

DATED : January 1, 1980

INVENTOR(S) : Kai Hansen

It is certified that error appears in the above-identified patent and that said Letters Patent are hereby corrected as shown below:

(Continued)

In the Specification:

Col. 1, line 68 and continuing onto Col. 2, line 1, "8-azaspiro..." should read --8-aza-spiro...--.

Col. 4, line 50, "$R_4$-O-CM=" should read --$R_4$-O-CH=--; and "$R_4$-O-CH=" should read --$R_4$-S-CH=--.

Col. 14, line 42, "3,63" should read --3.63--; and line 64, "(6,35 ml)" should read --(6.35 ml)--.

In the Claims:

Claim 3, (Col. 16, line 51), "acetic cid" should read --acetic acid--.

Signed and Sealed this

Tenth Day of June 1980

[SEAL]

Attest:

SIDNEY A. DIAMOND

Attesting Officer

Commissioner of Patents and Trademarks